US012654031B2

(12) United States Patent
Traneus et al.

(10) Patent No.: US 12,654,031 B2
(45) Date of Patent: Jun. 16, 2026

(54) RADIOTHERAPY TREATMENT PLAN EVALUATION AND IMPROVEMENT

(71) Applicant: RaySearch Laboratories AB (Publ), Stockholm (SE)

(72) Inventors: Erik Traneus, Uppsala (SE); Lars Glimelius, Stockholm (SE); Erik Engwall, Hagersten (SE); Elias Coniavitis, Stockholm (SE)

(73) Assignee: Raysearch Laboratories AB, Stockholm (SE)

( * ) Notice: Subject to any disclaimer, the term of this patent is extended or adjusted under 35 U.S.C. 154(b) by 0 days.

(21) Appl. No.: 18/681,084

(22) PCT Filed: Jun. 16, 2022

(86) PCT No.: PCT/EP2022/066509
§ 371 (c)(1),
(2) Date: Feb. 5, 2024

(87) PCT Pub. No.: WO2023/016683
PCT Pub. Date: Feb. 16, 2023

(65) Prior Publication Data
US 2025/0121208 A1 Apr. 17, 2025

(30) Foreign Application Priority Data
Aug. 13, 2021 (EP) ..................................... 21191208

(51) Int. Cl.
*G16H 20/40* (2018.01)
*A61N 5/10* (2006.01)
(52) U.S. Cl.
CPC ............. *A61N 5/103* (2013.01); *G16H 20/40* (2018.01)

(58) Field of Classification Search
None
See application file for complete search history.

(56) References Cited

U.S. PATENT DOCUMENTS 10,328,282 B2 * 6/2019 An ......................... A61N 5/1031
10,549,121 B2 * 2/2020 Wu ........................ A61N 5/1031
(Continued)

FOREIGN PATENT DOCUMENTS

CN 111921098 A 11/2020
EP 3228357 A1 10/2017
(Continued)

OTHER PUBLICATIONS

Chris McIntosh and Thomas G Purdie, "Voxel-based dose prediction with multi-patient atlas selection for automated radiotherapy treatment planning", Dec. 20, 2017, Physics in Medicine & Biology, vol. 62, No. 2. (Year: 2017).*
(Continued)

*Primary Examiner* — Robert A Sorey
(74) *Attorney, Agent, or Firm* — Noréns Patentbyrå AB

(57) ABSTRACT

A radiotherapy treatment plan may be evaluated based on a combination of two or more metrics, by the steps of simulating the result of delivery of the plan, obtaining values from the simulation for at least a first and a second metric, performing a multivariate analysis of the values and determining a quality of the plan based on the result of the multivariate analysis. The metrics may include at least one of dose, LET, track ends, RBE, alpha/beta ratio and statistical uncertainty of the plan.

8 Claims, 4 Drawing Sheets

(56)  References Cited

U.S. PATENT DOCUMENTS

| | | | | |
|---|---|---|---|---|
| 12,083,358 | B2 * | 9/2024 | Bengtsson | A61N 5/1038 |
| 2019/0076671 | A1 * | 3/2019 | Willcut | A61N 5/1038 |
| 2019/0255354 | A1 * | 8/2019 | Nordström | A61N 5/1031 |
| 2019/0329072 | A1 * | 10/2019 | Magro | A61N 5/1075 |
| 2019/0336790 | A1 | 11/2019 | Traneus et al. | |
| 2021/0220671 | A1 * | 7/2021 | Eriksson | A61N 5/1037 |
| 2023/0144962 | A1 * | 5/2023 | Andersson | A61N 5/103 |
| | | | | 378/65 |
| 2024/0091558 | A1 * | 3/2024 | Traneus | G16H 20/40 |
| 2024/0379211 | A1 * | 11/2024 | Voet | A61N 5/1031 |

FOREIGN PATENT DOCUMENTS

| | | | |
|---|---|---|---|
| EP | 3326694 | A1 | 5/2018 |
| JP | 2013248133 | A | 12/2013 |
| WO | 2016046683 | A2 | 3/2016 |

OTHER PUBLICATIONS

International Search Report & Written Opinion dated Sep. 16, 2022, European Patent Office, Rijswijk, Netherlands.

Santos Tania et al: "Evaluaiton of the complexity of treatment plans from a national IMRT/VMAT aud it—Towards a plan complexity score", Physica Medica, Acta Medica Edizioni E Congressi, Rome, IT, vo 1. 70, Jan. 23, 2020 (Jan. 23, 2020), pp. 75-84, XP086052974, ISSN: 1120-1797, DOI: 10.1016/J.EJMP.2020.01.015 [retrieved on Jan. 23, 2020].

Vandewouw Marlee M et al: "Robotic path-finding in inverse treatment planning for stereotactic radiosurgery with continuousdose delivery", Medical Physics, AIP, Melville, NY, US, vol. 43, No. 8, Jul. 15, 2016 (Jul. 15, 2016), pp. 4545-4557,XP012209347, ISSN: 0094-2405, DOI: 10.1118/1.4955177 [retrieved on Jul. 15, 2016].

Office action dated Sep. 11, 2024 from the European Patent Office, Munich, Germany.

Office action dated Nov. 25, 2025 in corresponding Japanese application No. 2024-517391, Japanese Patent Office, Tokyo, Japan.

1 Office Action in corresponding Chinese application No. 202280035512.4, Chinese Patent Office, Beijing, China.

* cited by examiner

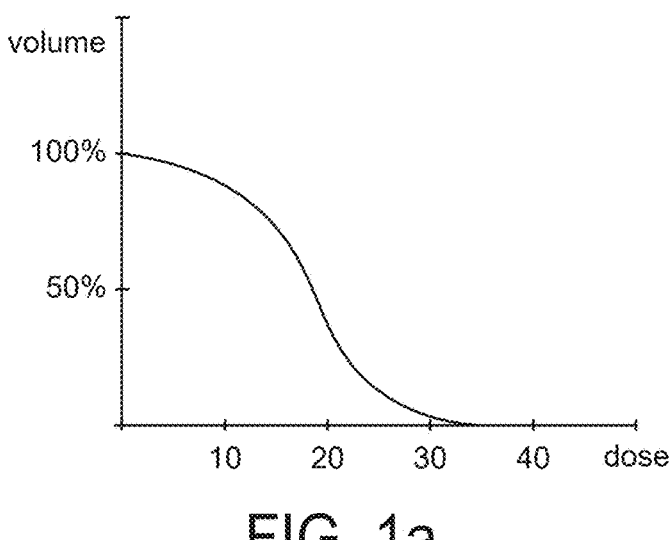
FIG. 1a
FIG. 1b
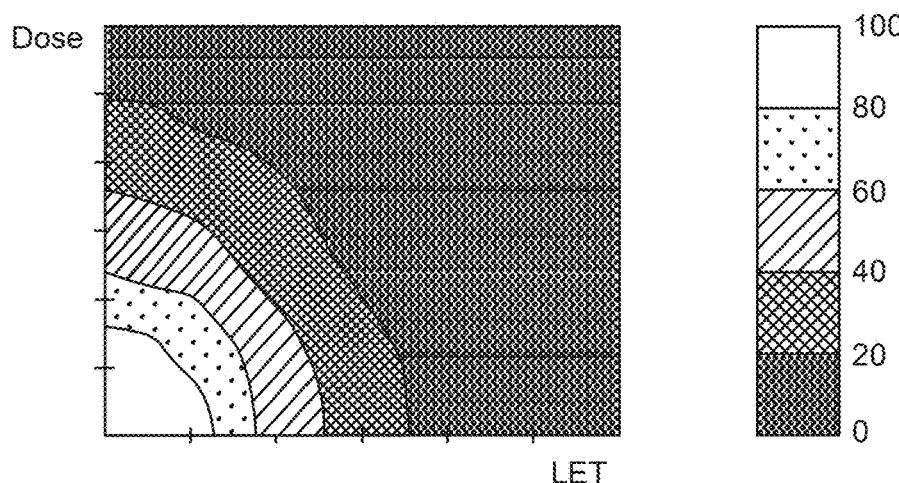
FIG. 2a

RADIOTHERAPY TREATMENT PLAN EVALUATION AND IMPROVEMENT

TECHNICAL FIELD

The present invention relates to a computer-based method of evaluating a radiotherapy treatment plan, a computer program product and a computer system for performing said method.

BACKGROUND

When developing a radiotherapy treatment plan for treating a patient, various factors such as patient anatomy and type of radiation are considered. Before a radiotherapy treatment plan can be delivered to a patient it must also be evaluated to determine if it will have the desired effect on the patient.

For evaluating a radiotherapy treatment plan, it is important to determine the dose distribution resulting from the plan and in particular the dose to regions of interest (ROI), such as the target and one or more organs at risk (OAR). Dose volume histograms (DVH) are commonly used to indicate, for the range of doses, the fraction of a certain region that receives at least a certain dose (a cumulative histogram), or a dose within certain limits (a differential histogram). This can be used, for example, to ensure that the plan will result in substantially the whole target receiving a dose above a certain minimum target dose and/or substantially all of an OAR receiving a dose that is below a maximum to ensure that the damage to the OAR is limited.

However, there are other factors than dose that also influence the effect of a certain plan on the patient. Such factors include Linear energy transfer (LET) and track ends. Treatment planning systems are increasingly enabling the monitoring of such other factors in addition to the dose.

It is an object of the present invention to provide an improved evaluation method for radiotherapy treatment plans.

SUMMARY OF THE INVENTION

The present disclosure relates to a computer implemented method for evaluating a radiotherapy treatment plan. The method includes
    simulating the result of delivery of the plan,
    obtaining values from the simulation for at least a first and
        a second metric
    performing a multivariate analysis of the values, and
    determining a quality of the plan based on the result of the
        multivariate analysis
    The metrics may include, for example, any combination of two or more of the following:
    physical dose
    RBE dose
    LET, for example in the form of a weighted average value
        such as a dose-weighted LET or a fluence-weighted
        LET
    RBE factors
    dose rate
    track-ends
    statistical uncertainty of the predicted dose
    the alpha/beta ratio, which reflects the tissue's sensitivity
        to radiation
    The evaluation result can be used to determine if the plan is appropriate for delivery to the patient. It can also be used to guide improvements to the plan.

The invention is based on the realization that different metrics interact to determine the effect of the treatment on the patient. For example, the damage caused by a specific dose will vary depending on the LET. Therefore, for example, a higher dose to a risk organ can be acceptable if the LET is low than if the LET is higher.

The multivariate analysis may be a bivariate analysis in which the relationship between two of the factors is determined. Preferably, but not necessarily, one of the factors considered is dose. A particularly useful combination determines the relationship between dose and LET.

Alternatively, three or more factors may be considered together in ways that will be discussed in more detail below.

The method preferably comprises the step of visualizing the relationship between the two or more metrics on a user display. This may be done, for a bivariate analysis, for example, in a 2D histogram in the form of a heat map or a 3D surface.

Subsequent steps may be performed based on the determined quality. Such subsequent steps may include whether or not the plan should be delivered to a patient, or deciding on an improvement of the plan to increase its quality.

The method may also include the step of setting upper and/or lower limits for one or both metrics and identifying any voxel having metrics that lie within these limits for both metrics. In this way, combinations of high values for two or more metrics that affect each other negatively may be avoided. By successive applications of this method with limits spanning the full range of possible values, it is possible to organize the information in a manner that facilitates further analysis. For example, the data may be organized in the form of a 2-dimensional volume histogram, where each bin corresponds to a combination of limits on the two metrics and the value of the bin corresponds to the number of voxels in a given region (and by extension, the proportion of the volume) that fulfill those limits. This procedure may be repeated for different sets of upper and lower limits for the metrics.

The disclosure also relates to a computer program product comprising computer-readable code means which when run in a processor will cause the processor to perform the method according to any one of the preceding claims. the code means may be stored in a memory unit, such as a non-transitory memory unit.

The disclosure also relates to a computer system comprising a processor and a program memory, said program memory holding a computer program product according to the above, to be run in the processor

BRIEF DESCRIPTION OF DRAWINGS

The invention will be described in more detail in the following, by way of examples and with reference to the appended drawings.

FIGS. 1a and 1b show a cumulative histogram and a differential histogram, respectively.

FIGS. 2a, 2b and 2c show different 2D representations of combinations of values.

DETAILED DESCRIPTION OF EMBODIMENTS

Figure 2B:
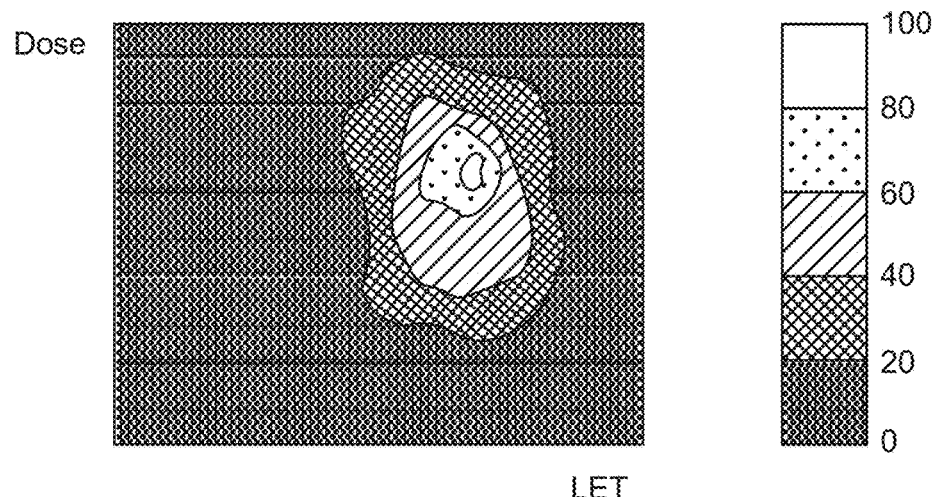

As explained above, the disclosure relates to correlating values for two or more relevant metrics for evaluating a radiotherapy treatment plan. This is advantageous because it acknowledges that different metrics may influence each other and therefore enables the combined effect of two or more metrics to be considered. Preferably, the metrics include two or more of the following:

Dose. The dose to various regions in the patient is an important factor for the outcome of the plan. The physical dose or the RBE weighted dose may be considered.

Dose rate. The dose rate can also affect the result of the plan. In particular, very high dose rates have been found to be advantageous in some situations.

Linear Energy Transfer (LET). The LET is the amount of energy that an ionizing particle transfers to the material traversed per unit distance. Hence a high LET is also often associated with an increased effect of the radiation.

Relative Biological Effectiveness (RBE) is an indicator of the biological effectiveness of the type of radiation used in the plan.

Track-ends, that is, the position where individual particles deposit the last of their energy and stop. The LET is higher close to the track end, which means that a high number of track ends implies a high LET statistical uncertainty (or Monte Carlo uncertainty) on the Monte Carlo-based dose calculation. High statistical uncertainty in regions of low dose is tolerable, while having high statistical uncertainty in clinically relevant regions may require a repetition of the dose calculation with higher accuracy. A user may want to avoid doing this routinely since it is time-consuming. A clinically relevant region may be, for example, a region with high values of dose or other interesting metric.

Ratio alpha/beta. This ratio is indicative of the sensitivity of an organ to radiation.

Combinations including dose as one metric are particularly suitable, and a preferred embodiment involves a bivariate analysis of dose and LET. Other suitable combinations include the following:

MC-calculated dose and MC-uncertainty. The relationship between dose and uncertainty may be significant because a high degree of uncertainty may be acceptable if the dose is low but more problematic if the dose is high.

Dose and "dirty" dose. A dirty dose is a dose that has been deposited with an LET above a certain threshold value.

Dose computed with one RBE-model and dose computed with a different RBE model. In this case the analysis may identify areas where a variation in the RBE may be problematic, for example if a simple RBE model is used and there is a desire to consider a more refined model as well. This is particularly relevant for risk organs.

Dose rate and oxygenation level. The oxygenation level is important for the FLASH effect, and should be considered in particular for risk organs.

FIG. 1a is a schematic example of a cumulative dose volume histogram (DVH), with volume along the Y axis and dose along the X axis. The curve indicates the fraction of the volume that has received at least the corresponding dose. As can be seen, 100% of the volume has received at least 0 Gy, with the volume decreasing as the dose increases.

FIG. 1b is a schematic example of a differential DVH, again with volume along the Y axis and dose along the X axis. In this case, the dose is divided into dose bins of, in this case, 10 Gy each, and the histogram shows the fraction of the volume that has received a dose within each bin.

As will be understood, the same type of histogram can be obtained for other metrics as well, for example for LET. Each histogram is one-dimensional and displays volume data for one metric. It should be noted that such a histogram only displays the fraction, or size, of the volume and not the actual distribution within the volume, that is, which part of the volume has received which dose.

FIG. 2a is an example of a simplified cumulative 2D histogram designed to display the fraction of the volume having each combination of x and y values. In this example, the size of the area is displayed as a sequence of patterns; in a real implementation normally a color scale will be used. A block to the right of the diagram indicates the size of area corresponding to each pattern. As can be seen, the combinations of x and y values that apply to a large volume or fraction of the region of interest have a bright pattern, and a decreasing fraction is matched by a gradually darker pattern. Specifically, almost 100% of volume has values for both dose and LET, that are higher than 5 Gy and 20 keV/µm, respectively, whereas a very small fraction of the volume has values close to the maximum for both dose and LET.

In the example shown in FIG. 2a, the dose is displayed along the Y axis and the LET is displayed along the X axis, but this type of diagram may be provided for any combination of two variables.

FIG. 2b is an example of a simplified differential 2D histogram designed to display the size of the volume having a value on the X axis, representing dose in this example, and a value on the Y axis, representing LET, that are within certain ranges, for example x within the range [a,a') and y within the range [b,b'). In this example, as in FIG. 2a, the size of the volume that is within each range, is displayed as a sequence of patterns; in a real implementation normally a color scale will be used. A block to the right of the diagram indicates the size of volume corresponding to each pattern. As can be seen the area having both a high dose and a high LET is relatively small.

Figure 2C:
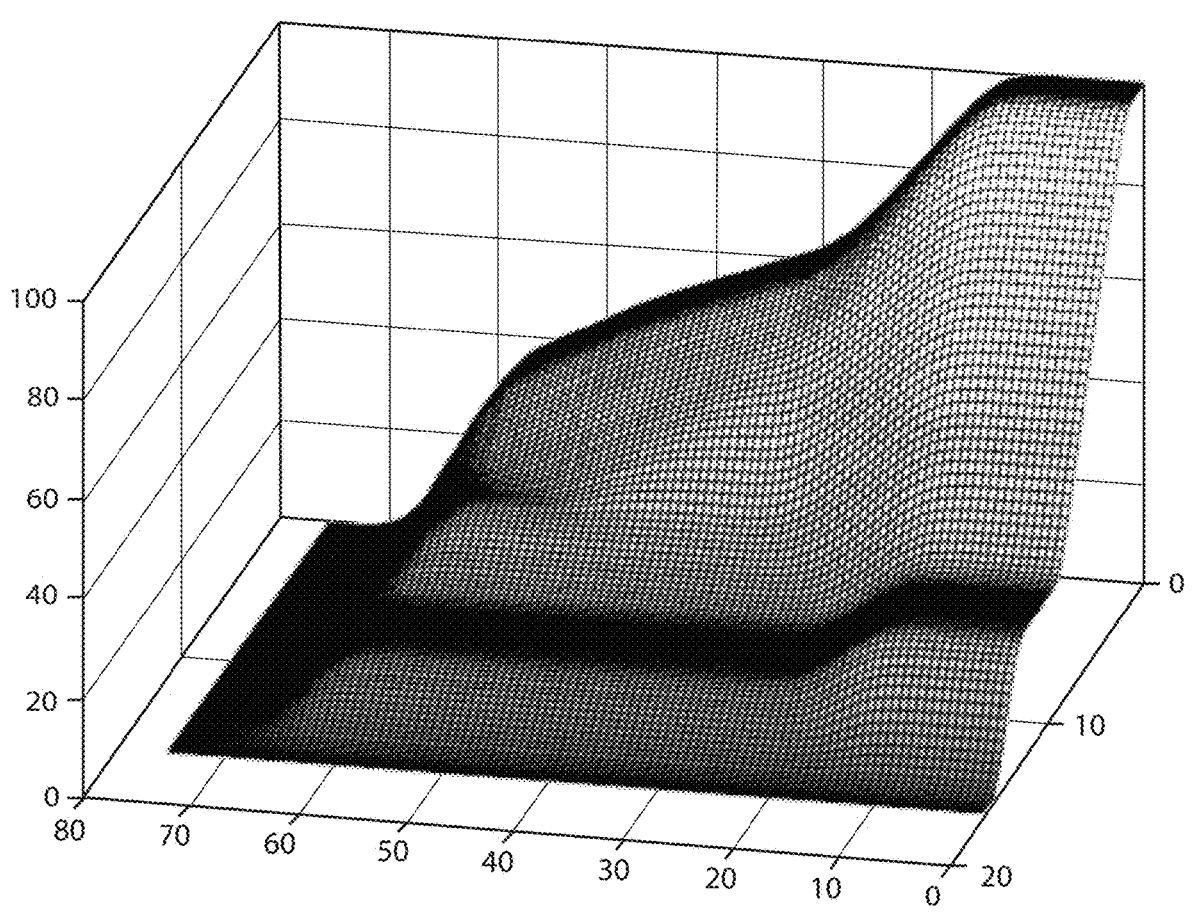

FIG. 2c is a different example of a cumulative 2D histogram in which a rotatable 3D surface is used to indicate the size or fraction of the area. The height of the 3D surface in any (x,y) point represents the size of the area that has that combination of values for x and y. Differential 2D histograms may also be displayed as surfaces. How to do this is known per se.

Each of the diagrams in FIGS. 2a, 2b and 2c is of a type well known as such and is helpful in this context for the user to identify if there is a large portion of the volume where both the displayed metrics have unfavorable values, for example, where both the dose and the LET are high.

Figure 3:
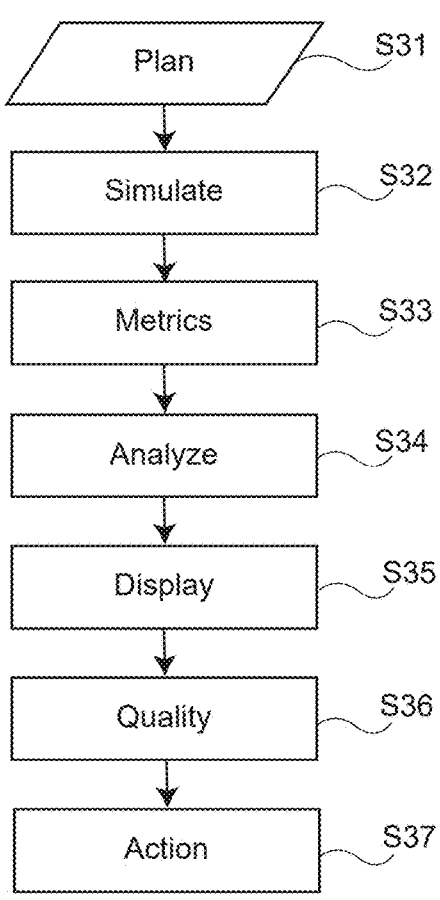
FIG. 3 is a flow chart of a method according to the present invention.

FIG. 3 is a flow chart of an overall method according to embodiments of the invention. Input data S31 to the method include a treatment plan that has already been obtained in a suitable way, for example by optimization. In step S32, a simulation of the plan is performed to determine a predicted result of the delivery of the plan, the predicted result including values for at least a first and a second metric. In step S33, values for least a first and a second metric is obtained from the predicted result and in step S34 the metrics are analyzed by a multivariate analysis method. If two different metrics are used the multivariate analysis is a bivariate analysis. In an optional step S35, the result of the multivariate analysis is displayed, for example in the form of one or more diagrams as illustrated in FIGS. 2a, 2b and 2c.

The result of the analysis is used, in step S36, to determine the quality of the plan, which may in turn be used in step S37 to determine a subsequent action. The action may be to deliver the plan to the intended patient, if the quality is determined to be high enough, or to discard the plan and obtain a new one. The action may also be to improve the existing plan and possibly to re-evaluate the improved plan.

Figure 4:
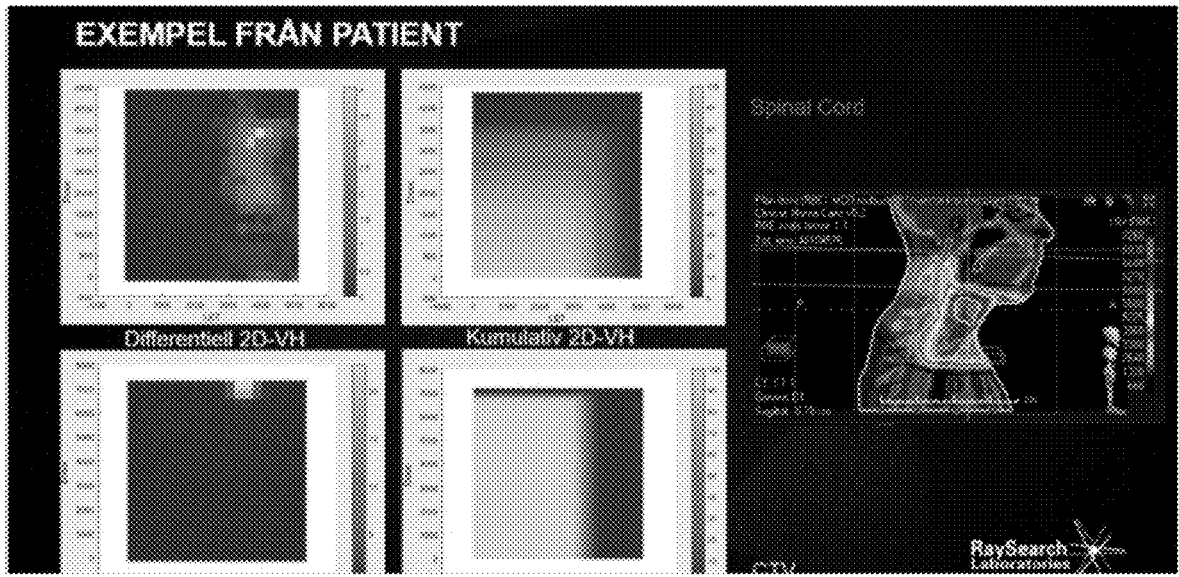
FIG. 4 illustrates a possible use of the analysis performed according to embodiments of the invention.

The display of the metrics in diagrams as discussed above is preferably enhanced by the possibility to choose one or more areas in the diagrams to identify the corresponding voxels in the dose-view. This means that an operator can select, for example, an area of the diagram that indicates an unfavorable combination of metrics, and the system will identify the voxels in the dose view that have this combination. This function is visualized in FIG. 4, using a heat map as an example. To the left in FIG. 4 is a 2D heat map like the one shown in FIG. 2a. The operator has identified an area in the heat map, where a<A<a' and b<B<b'. To the right in FIG. 4 is a corresponding dose view in which only the voxels fulfilling this condition are shown. This enables the user to identify the areas within the patient that will have the unfavorable combination of metrics in this example, which will make it easier to evaluate the importance of this to the quality of the plan. While the visualization shown in FIG. 4 is helpful to an operator, the analysis underlying the diagrams could be performed without creating the diagrams and may be used for automatic evaluation by the system.

It is worth noting that, for the cumulative view of the 2D-VH, taking the "cross-section" of the histogram along the A-axis at B=0 will result in the regular one-dimensional volume histogram for metric A, that is, a regular DVH if the metric is Dose). Similarly taking the "cross-section" along the B-axis at A-a' results in the one-dimensional volume histogram for metric B subject to A>a' (for example, a LET-VH for dose>a'). Preferably, the system should allow the user to take such cross-sections (shown as regular one-dimensional histograms) at whichever points are of interest. These one-dimensional volume histograms could be plotted in the same graph as a 3-dimensional surface, if that mode of plotting is chosen.

It is also possible to perform a multi-variate analysis, accounting for more than the two metrics plotted. One could introduce cuts on one or more additional relevant metrics and then plot the 2D-VH, and any "cross-sections" of interest, accounting only for voxels passing those cuts. For example, one may want to investigate a 2D-VH for Dose and LET only for certain regions of alpha/beta.

It should also be possible to plot more than one 3-dimensional surfaces at the same time, where the different 2D-VH surfaces could for example come from:

Different regions selected through cuts on a third metric (e.g. high, intermediate, and low alpha/beta).

Displaying the 2D-VH surface only within a certain value range of the third metric.

Different plans that a user wishes to compare.

Different scenarios in the context of robust evaluation, allowing the user to visualize the range of variation between them.

The visibility of the different surfaces could be toggled on/off for easier inspection.

It should further also be possible to extract clinical goals from a 2D-VH. Some samples of such possible clinical goals, in the example of a 2D-VH of dose and LET, could be:

First determine a dose-at-volume level (e.g. D2, D50, D98) and then set a clinical goal for the LET, for doses above/below this dose level.

A requirement on the maximum percentage of the volume that is allowed to be above certain thresholds on dose and LET, for example max X % of the volume may lie above both Dose>a and LET>b A requirement on the maximum of dose and LET at a certain percentage of the volume, for example max X dose and max Y LET at v % of the volume)

The system may be arranged to determine whether each goal is achieved or not.

An example of a method of evaluating a plan will be described in the following based on a bivariate analysis involving dose and LET: First the user selects a low dose threshold below which the LET does not need to be considered. The user then selects a limit for maximum acceptable LET. In response to this, the system displays the dose for the voxels in which the dose is above the dose threshold and the LET is also above the limit. Either the system returns the volume corresponding to the voxels that have values above both the threshold and the limit, or these voxels are indicated in a suitable way in an image, for example by use of color. Instead of dose and LET, any combination of the metrics listed above may be used, including the following:

RBE factors and the dose in a risk organ, may be considered because a combination of high RBE factor and high dose will result in a high biological dose which is undesired in a risk organ.

High dose rate and risk organ doses for FLASH therapy may be considered to ensure that the dose rate is sufficiently high for achieving the FLASH effect.

High EPID gammas and high dose in a risk organ. A high deviation combined with a high dose is undesirable. If the dose is low, the gamma value is less important.

Figure 5:
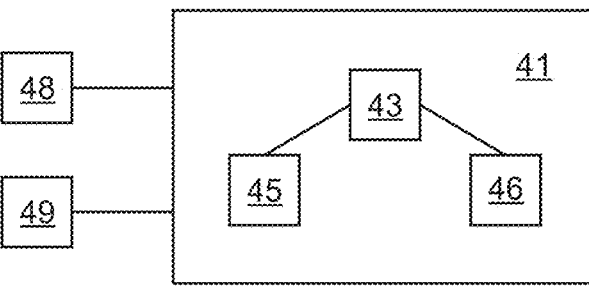
FIG. 5 is a schematic representation of a computer in which the inventive methods may be performed.

FIG. 5 is a schematic overview of a computer system in which the optimization according to the invention may be carried out. A computer 41 comprises a processor 43, a data memory 45 and a program memory 46. Preferably, one or more user input means 48, 49 is also present, in the form of a keyboard, a mouse, a joystick, voice recognition means and/or any other available user input means. The user input means may also be arranged to receive data from an external memory unit. The data memory includes either the relevant metric values and/or input data required to calculate such values. This typically includes patient data and characteristics of the delivery machine. The program memory comprises a computer program arranged to perform a method according to an embodiment of the present invention, for example as discussed in connection with FIG. 3. As is common in the art, one or more data memories and one or more program memories may be used, and all or some of the data and/or the program may be found in external units and obtained as needed through conventional communication devices.

The invention claimed is:

1. A computer-based method of evaluating a radiotherapy treatment plan, comprising:

simulating a predicted result of delivery of the plan to obtain per-voxel for at least a first and a second metric for a treatment volume, wherein the first metric is related to dose, and wherein the second metric is one of the following: LET, dirty dose, track ends, RBE, alpha/beta ratio, and statistical uncertainty;

analyzing the obtained per-voxel values, the analyzing including segmenting the treatment volume by defining a first interval for the first metric and a second interval for the second metric, and assigning to a segment the voxels whose values for both metrics fall within the respective intervals;

evaluating a quality of the plan by comparing at least one condition expressed in terms of the voxel segmentation to a corresponding clinical goal; and in response to the evaluation, performing a workflow action selected from: delivering radiation therapy in accordance with the plan to a patient, modifying the plan, and discarding the plan.

2. The method of claim 1, wherein presenting a visual representation includes:

visualizing the identified voxels in an image.

3. The method of claim 2, further comprising identifying in the image the voxels associated with a user-selected region.

4. A non-transitory computer program product, comprising a computer readable storage medium having program instructions embodied therewith, the program instructions being executable by a processor to cause the processor to perform the method of claim 1.

5. The method of claim 1, wherein:

the analyzing further comprises generating, from the per-voxel values, a two-dimensional volume histogram that represents a distribution of voxel counts over intervalizations of the first and second metrics; and the evaluating comprises comparing at least one condition expressed in terms of the two-dimensional volume histogram to the clinical goal.

6. The method of claim 5, wherein the clinical goal specifies a limit on a proportion of voxels within a defined interval pair of the two-dimensional volume histogram.

7. The method of claim 1, wherein modifying the plan comprises repeating the simulation with increased accuracy when statistical uncertainty exceeds a threshold in a clinically relevant region.

8. A computer system comprising a processor and a program memory, the program memory containing instructions that when executed by the processor causes the processor to perform a method of evaluating a radiotherapy treatment plan including the following steps:

simulating a predicted result of delivery of the plan to obtain per-voxel values for at least a first and a second metric for a treatment volume, wherein the first metric is related to dose, and wherein the second metric is one of the following: LET, dirty dose, track ends, RBE, alpha/beta ratio, and statistical uncertainty;

analyzing the obtained per-voxel values, the analyzing including segmenting the treatment volume by defining a first interval for the first metric and a second interval for the second metric, and assigning to a segment the voxels whose values for both metrics fall within the respective intervals;

evaluating a quality of the plan by comparing at least one condition expressed in terms of the voxel segmentation to a corresponding clinical goal; and in response to the evaluation, performing a workflow action selected from: delivering radiation therapy in accordance with the plan to a patient, modifying the plan, and discarding the plan.

* * * * *